(12) United States Patent
Wotton, III (10) Patent No.: US 8,495,902 B2
(45) Date of Patent: Jul. 30, 2013

(54) CRIMPING DEVICE

(75) Inventor: Harold M. Wotton, III, Woodstock, CT (US)

(73) Assignee: MWI Veterinary Supply Co., Meridian, ID (US)

( * ) Notice: Subject to any disclaimer, the term of this patent is extended or adjusted under 35 U.S.C. 154(b) by 68 days.

(21) Appl. No.: 13/135,665

(22) Filed: Jul. 12, 2011

(65) Prior Publication Data

US 2012/0131983 A1  May 31, 2012

Related U.S. Application Data

(60) Provisional application No. 61/458,695, filed on Nov. 30, 2010.

(51) Int. Cl.
    B21D 15/02 (2006.01)
    B21F 15/06 (2006.01)

(52) U.S. Cl.
    USPC .................. 72/409.01; 7/127; 7/128

(58) Field of Classification Search
    USPC ............. 72/409.01, 409.06, 409.11, 409.14, 72/409.19; 7/5.4, 4.6, 127, 128, 157
    See application file for complete search history.

(56) References Cited

U.S. PATENT DOCUMENTS

| | | | | |
|---|---|---|---|---|
| 273,382 | A * | 3/1883 | Packham | 72/409.19 |
| 354,657 | A * | 12/1886 | Rowe | 72/409.01 |
| 1,066,804 | A * | 7/1913 | Falk | 72/409.01 |
| 2,583,625 | A * | 1/1952 | Bergan | 72/409.19 |
| 3,531,971 | A | 10/1970 | Robb et al. | |
| 3,694,834 | A * | 10/1972 | Daniels, Jr. | 7/133 |
| 3,808,870 | A * | 5/1974 | Blancett | 72/413 |
| 3,903,725 | A * | 9/1975 | Rommel | 72/409.09 |
| 4,637,084 | A * | 1/1987 | Wood | 7/134 |
| 5,042,285 | A | 8/1991 | Levy | |
| 5,263,355 | A * | 11/1993 | Malagnoux | 72/409.09 |
| 5,604,947 | A * | 2/1997 | Bates et al. | 7/133 |
| 5,913,933 | A * | 6/1999 | Beetz et al. | 72/409.16 |
| 6,152,188 | A | 11/2000 | Barlasov | |
| 6,395,010 | B1 | 5/2002 | Wotton, III | |
| 6,910,363 | B2 * | 6/2005 | Beetz et al. | 72/409.14 |
| 7,121,307 | B2 | 10/2006 | Nasiatka et al. | |
| 2006/0156784 | A1 | 7/2006 | Reedy et al. | |
| 2009/0248063 | A1 | 10/2009 | Wotton, III | |

OTHER PUBLICATIONS

Written Opinion of the International Searching Authority, PCT Application No. PCT/US2011/001502, mailed Feb. 14, 2012, 4 pgs. (unnumbered).

* cited by examiner

*Primary Examiner* — David B Jones
(74) *Attorney, Agent, or Firm* — Iandiorio Teska & Coleman, LLP (57) ABSTRACT

A crimping device including a first jaw having, across its width and extending at least partially along its length, spaced multiple crimp members. A second jaw also includes, across its width and extending at least partially along its length, spaced multiple crimp members. Multiple crimps are created in a crimp tube when the first and second jaws are brought together about the crimp tube using a first handle for the first jaw and a second handle for the second jaw.

17 Claims, 7 Drawing Sheets

CRIMPING DEVICE

RELATED APPLICATIONS

This application claims benefit of and priority to U.S. Provisional Application Ser. No. 61/458,695 filed Nov. 30, 2010 incorporated herein by this reference.

FIELD OF THE INVENTION

The subject invention relates to crimping devices typically used in connection with crimp tubes used in medical and veterinary procedures.

BACKGROUND OF THE INVENTION

Crimping devices are used in procedures such as cruciate ligament stabilization where two ends of a suture (e.g., a mono-filament) are held together in a crimp tube or clamp). See U.S. Pat. No. 6,395,010 and U.S. Patent Publication No. 2009/0248063 incorporated herein by this reference.

It is important that the crimping action be precise. Too much pressure on the suture can cause breakage of the suture. If the crimp tube is not deformed enough, on the other hand, the suture can slip in the crimp tube. The above references disclose inventive crimping devices with spaced opposing crimping members. Each crimping action of these devices results in a single crimp in the crimp tube. Known devices for forming multiple crimps are large, complex, and involve multiple jaws. See U.S. Pat. Nos. 7,121,307; 6,152,188; and U.S. 2006/0156784 incorporated herein by this reference.

BRIEF SUMMARY OF THE INVENTION

It is necessary to provide more than one crimp in a crimp tube. When using the crimping tools of the prior art, the first crimp must be made, the tool then relocated to another location on the crimp tube in order to make a second crimp, and so on. Each change of tool location lends itself to errors.

The invention results from the at least partial realization that, in one preferred embodiment, a crimping device designed with first and second jaws each including multiple but offset crimping members results in a crimp tube with a tortuous internal channel providing a suture holding strength stronger than a prior art crimping tool but requiring only a single crimping action as opposed to multiple crimping actions.

The invention features a crimping device comprising a first moveable jaw having, across its width and extending at least partially along its length, spaced multiple fixed deformation or crimp members. A second moveable jaw also includes, across its width and extending at least partially along its length, spaced multiple fixed crimp members.

An engineered crimp pattern is created in a crimp tube when the first and second jaws are brought together about the crimp tube. There is a first handle for the first jaw and a second handle for the second jaw configured to close the jaws about a crimp tube.

Preferably, the crimp members of the first jaw are offset from the crimp members of the second jaw. In one design, the first jaw has first, second, and third crimp members and the second jaw has first and second crimp members. The second crimp member of the first jaw and the first and second crimp members of the second jaw have greater rounded protrusions. The first and third crimp members of the first jaw have smaller rounded protrusions.

In some embodiments, there is a first depression between the first and second crimp members and a second depression between the second and third crimp members of the first jaw. In this design, the first crimp member of the second jaw may oppose the first depression of the first jaw and the second crimp member of the second jaw may oppose the second depression of the first jaw. In some embodiments, there is a first depression on one side of the first crimping member of the second jaw, a second depression between the first crimp member and the second crimp member of the second jaw, and a third depression on an opposite side of the second crimp member of the second jaw. In such a design, the first crimp member of the first jaw opposes the first depression of the second jaw, the second crimp member of the first jaw opposes the second depression of the second jaw, and the third crimp member of the first jaw opposes the third depression of the second jaw.

The first and second jaws may further include first and second stop members defining a predefined gap between the crimp members of the first jaw and corresponding depressions of the second jaw and between the crimp members of the second jaw and the corresponding depressions of the first jaw when the jaws are fully closed.

The handles may connect to the jaws via a multi action mechanism. In one preferred version, the first handle includes a linkage pivotably connected between the first and second handle portions and the first handle portion of the first handle is pivotably connected to the second handle and the second handle portion of the first handle is pivotably connected to the second handle.

A method in accordance with the invention includes providing a first jaw having, across its width and extending at least partially along its length, spaced multiple crimp (engineered design) members and providing a second jaw having, across its width and extending along its length, spaced multiple crimp members creating multiple crimps in a crimp tube when the first and second jaws are brought together about the crimp tubes. A first handle is provided for the first jaw and a second handle is provided for the second jaw. The first handle may include a linkage pivotably connected between a first handle portion which is pivotably connected to the second handle and a second handle portion which is pivotably connected to the second handle.

One crimping device includes a first jaw having, across its width and extending at least partially along its length, first, second, and third crimp members with a depression between the first and second crimp members and between the second and third crimp members. A second jaw has, across its width and extending at least partially along its length, first and second crimp members with a depression therebetween. The first and second crimp members of the second jaw each oppose the depressions of the first jaw and the second crimp member of the first jaw opposes the depression in the second jaw.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
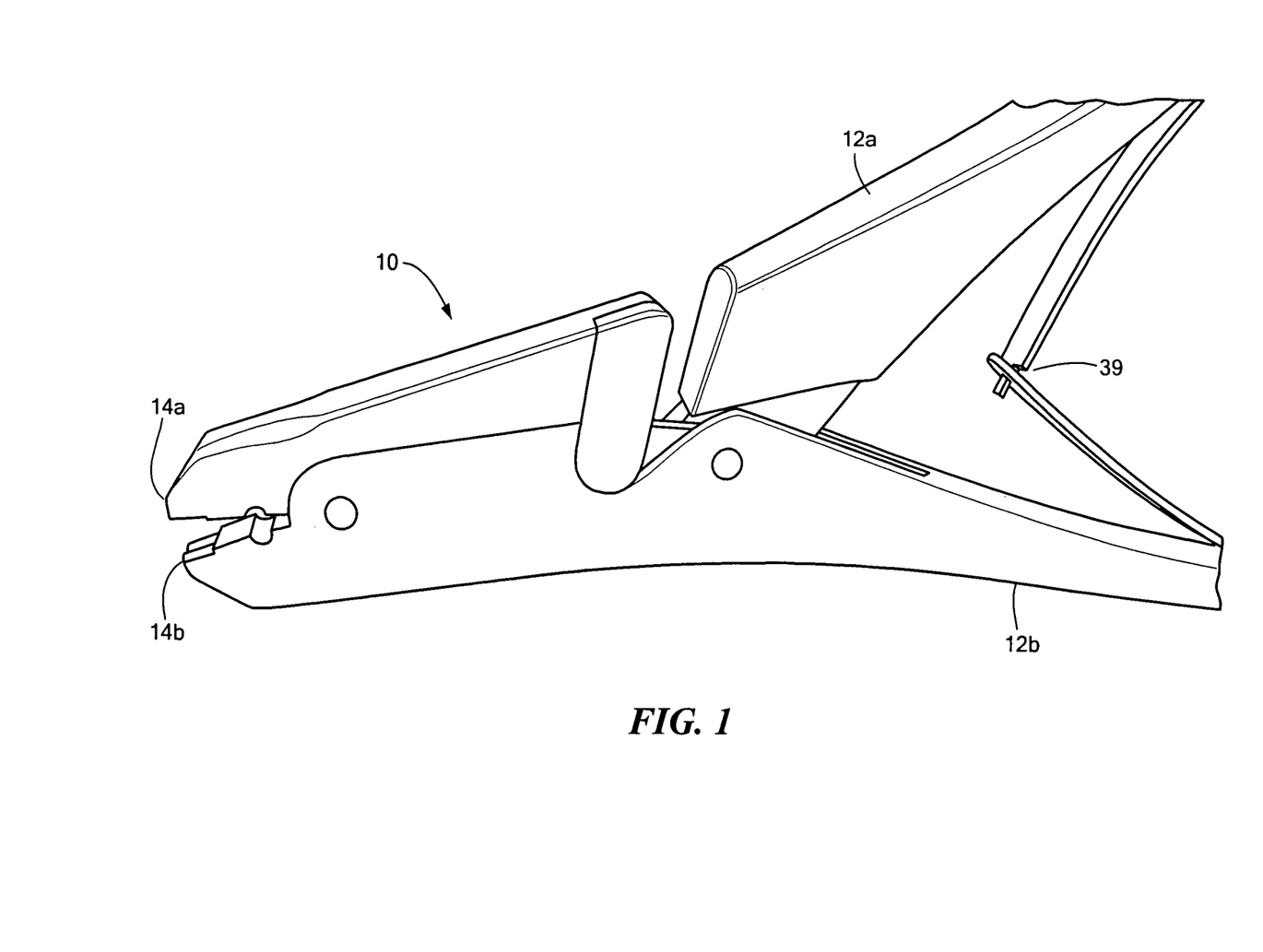
FIG. 1 is a schematic three-dimensional side view of an embodiment of a crimping tool in accordance with one example of the invention.
Figure 2:
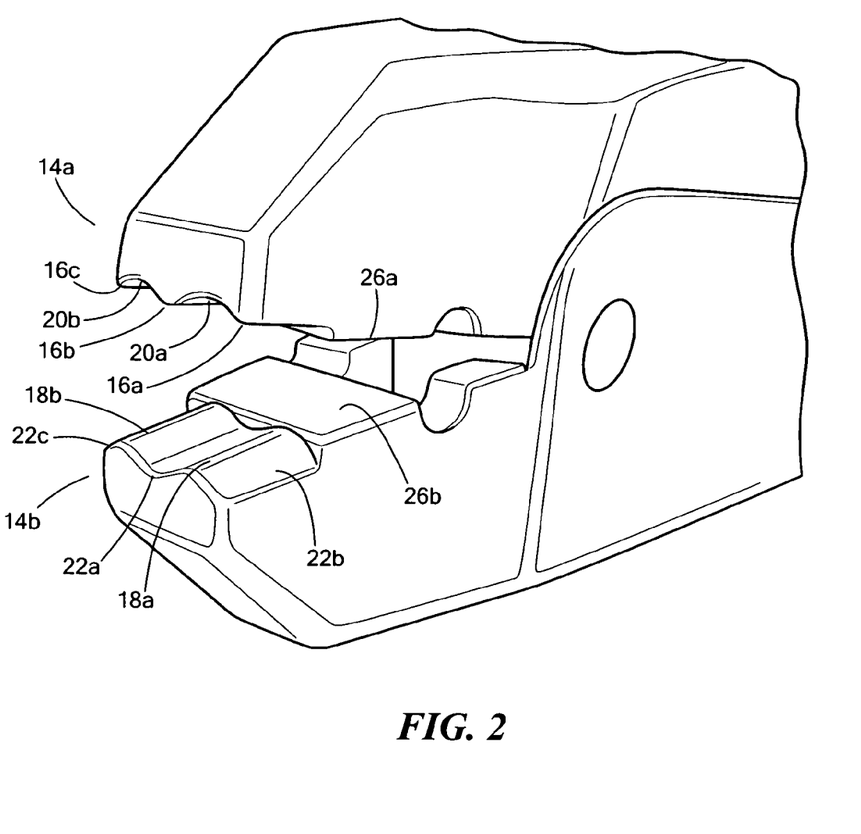
FIG. 2 is a schematic three-dimensional enlarged view of the crimping jaws of the tool shown in FIG. 1.
Figure 3:
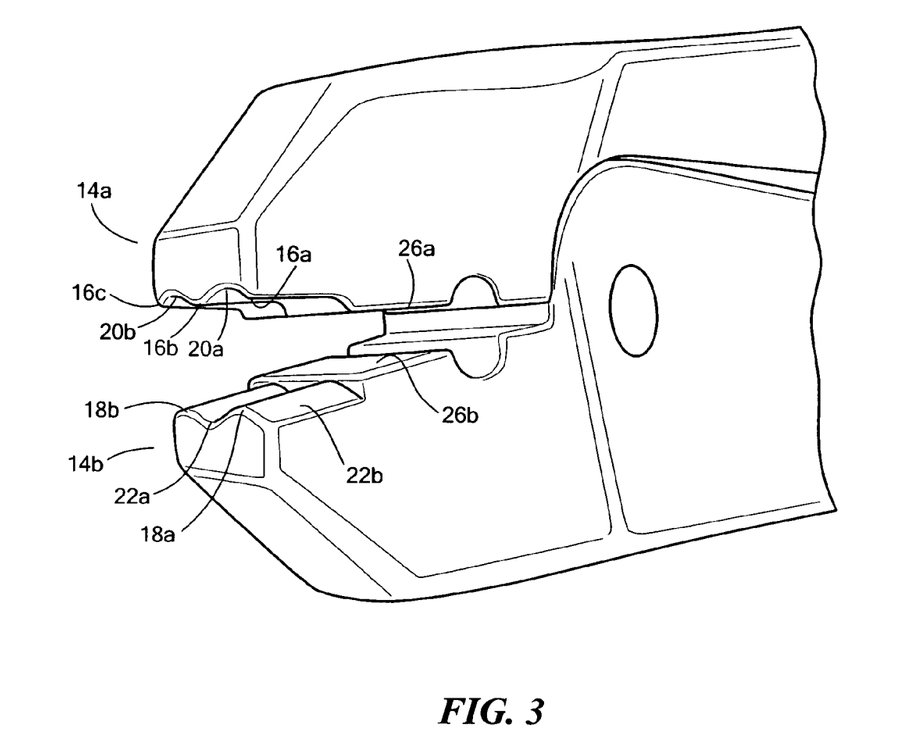
FIG. 3 is another schematic enlarged view of the crimping jaws of the crimping tool shown in FIGS. 1-2.
Figure 4:
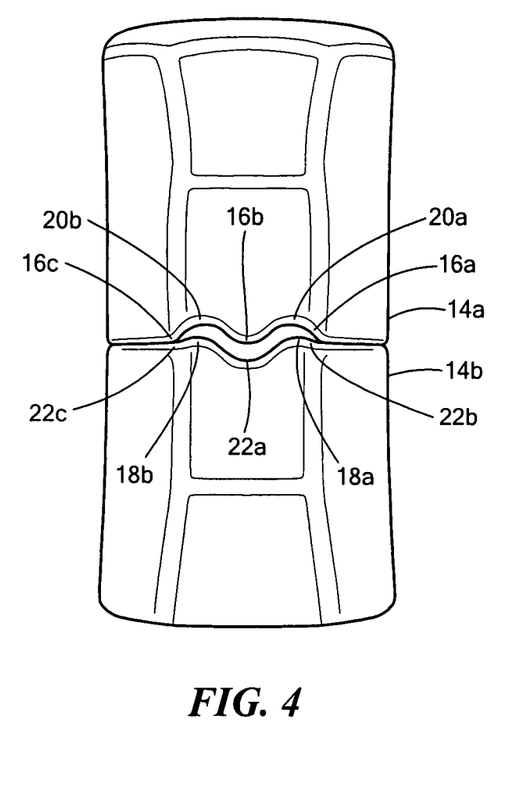
FIG. 4 is a schematic front view of the crimping jaws shown in FIGS. 1-3.
Figure 7:
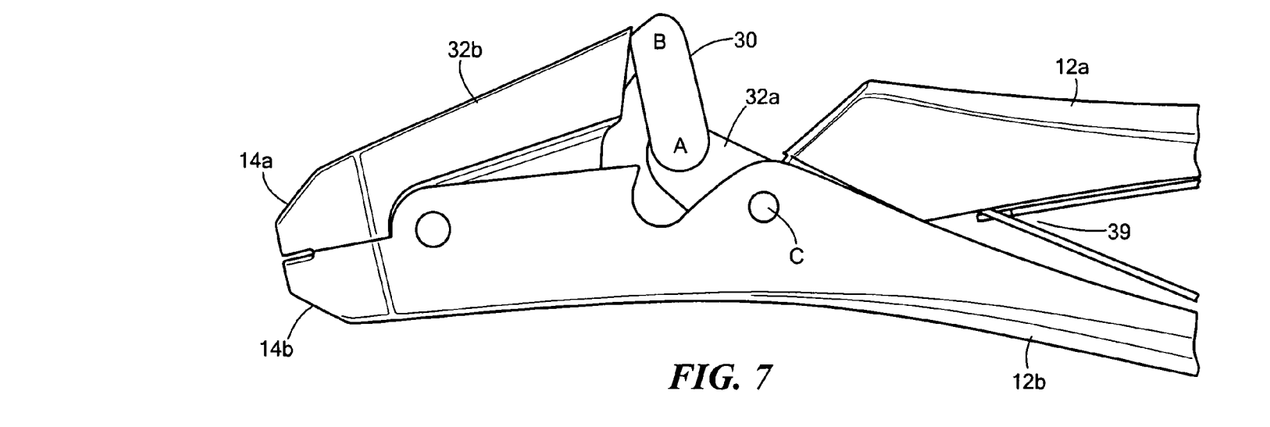
FIG. 7 is a schematic side view of the other side of the crimping tool of FIG. 1.
Figure 8:
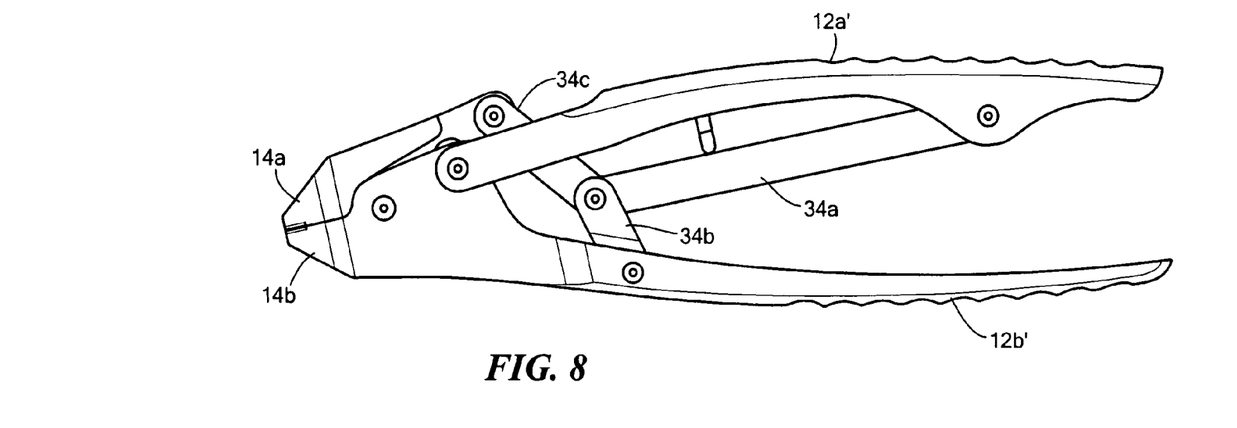
FIG. 8 is a side view of another crimp tool.

FIG. 1 depicts an embodiment of crimping tool 10 in accordance with the invention with first handle 12a, first jaw 14a and second handle 12b, and second jaw 14b. FIG. 7 shows the other side of the tool and FIG. 8 shows another tool design. FIGS. 2-4 better depict moveable jaws 14a and 14b each including, across their widths, integral, spaced multiple fixed in place crimping member formations. In this specific example, first jaw 14a has deformation or crimping member 16a, deformation or crimping member 16b, and deformation or crimping member 16c. Second jaw 14b has deformation or crimping member 18a and deformation or crimping member 18b. All of the crimping members extend at least partially along the length of their respective jaws as shown and the crimping members of jaw 14a are preferably offset from the crimping members of jaw 14b across the width of their respective jaws. Also, in this example, crimping members 16b, 18a, and 18b have a more rounded configuration while crimping members 16a and 16c have a less rounded configuration. Crimping members 18a, 18b, and 16b may comprise a full arc of material while crimping members 16a and 16c may comprise a ½ arc of material.

In this example, lengthwise depression 20a is between crimping members 16a and 16b and lengthwise depression 20b is between crimping members 16b and 16c. Depression 22a is between crimping members 18a and 18b, depression 22b is to the right (in the figures) of crimping member 18a, and depression 22c is to the left (in the figures) of crimping member 18b. Also, crimping member 16a of jaw 14a generally opposes depression 22b of jaw 14b, crimping member 16b generally opposes depression 22a, crimping member 16c generally opposes depression 22c while crimping member 18a of jaw 14b generally opposes depression 20a in jaw 14a and crimping member 18b generally opposes depression 20b.

Figure 5:
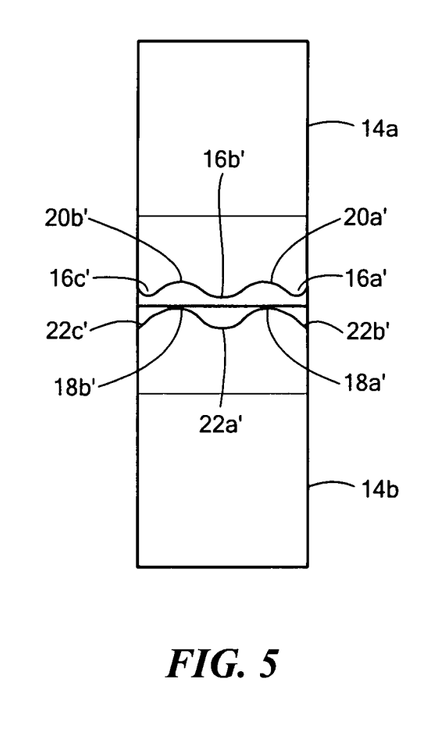
FIG. 5 is a schematic end view showing one design of a pair of crimping jaws in accordance with another example of the invention.
Figure 6:
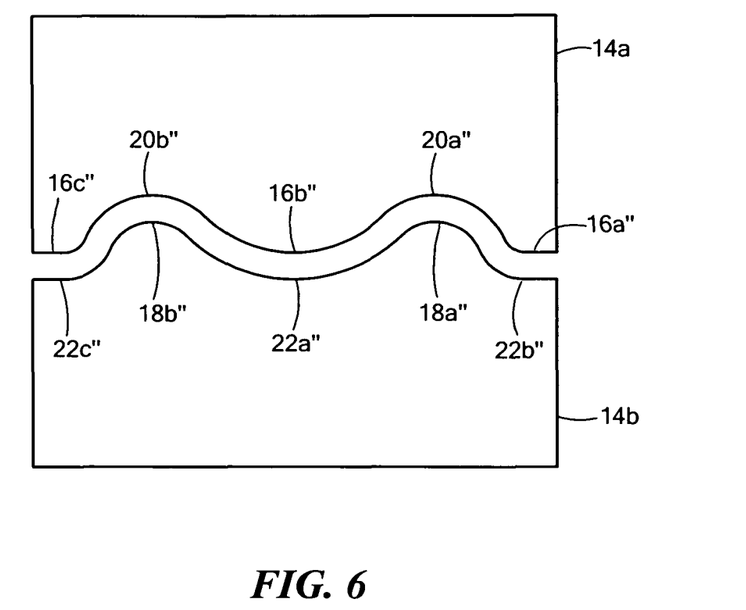
FIG. 6 is a schematic view showing another pair of crimping jaws.

Jaw 14a, FIG. 3 has stop member or flat 26a and jaw member 14b has stop member or flat 26b configured such that when jaws 14a and 14b are fully closed by the action of handles 12a and 12b, there is a predefined space or gap between the crimping members 16a, 16b, and 16c in jaw 14a and the corresponding depressions in second jaw 14b (depressions 22b, 22a, and 22c) and between crimping members 18a and 18b of jaw 14b and their corresponding depressions in first jaw 14a (depressions 20a and 20b). In one preferred embodiment, this gap is between 0.03 to 0.07 inches (e.g., 0.05 inches). Other multiple crimping member configurations are also possible. In one preferred example, FIG. 5, deformation members 16c' and 16a' had a radius of 0.015", deformation member 16b' had a radius of 0.045", and deformation members 18b' and 18a' had a radius of 0.055". Depressions 20b' and 20a' has a radius of 0.050". FIG. 6 shows a more symmetrical design where, for example, member 18b" mirrors depression 20b". This designed turned out to be, in testing, less optimal than the design of FIG. 5 where it can be seen that deformation member 18b", for example, is offset laterally from depression 20b'.

FIG. 7 shows an embodiment where handle 12a includes linkage 30 pivotably connected to first and second handle portions 32a and 32b via pins at locations A and B. First handle portion 32a is pivotably connected to second handle 12b at location C via a pin and second handle portion 32b is pivotably connected to second handle 12b at location D. Spring member 39, FIG. 1 biases the handles apart from each other. This design allows the surgeon to make multiple crimps simultaneously with little effort. In another embodiment, the double action handles of U.S. Pat. No. 6,395,010 may be used. Other handle configurations are possible. FIG. 8, for example, shows a handle design with handles 12a' and 12b' and linkages 34a, 34b, and 34c.

FIGS. 9A-9D show crimp tube 40 and within it two suture portions 42a and 42b. After the crimping tool shown in FIGS. 1-5 is used, spaced deformations 50a, 50b, and 50c are formed on one side of tube 40 due to the action of crimping member formations 16a'-16c' of jaw 14a, FIG. 5 and offset deformations 52a' and 52b' are formed in the opposite side of crimp tube 40, FIG. 9B due to the action of crimping member formations 18a' and 18b', FIG. 5. A similar engineered crimp pattern is attainable with the design of FIGS. 2-4.

The result is multiple deformations of the crimp tube at spaced locations, deformation of the suture at those locations, a tortuous path or channel within the crimp tube which locks the suture portions within the crimp tube, and for an engineered crimp pattern.

In testing, the holding strength was 457N or stronger which is comparable or stronger to the holding strength of using a prior art crimp tool. But, using the crimp tool of the subject invention, multiple crimps are made simultaneously as opposed to the need, with a prior art crimper, to reposition it three times to make three crimps.

Figure 9A:
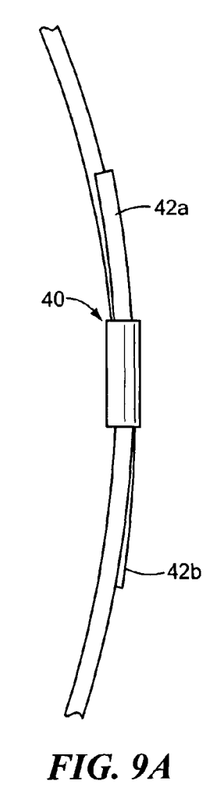
FIG. 9A is a schematic side view of a crimp tube before deformation and including the ends of a suture therethrough.
Figure 9B:
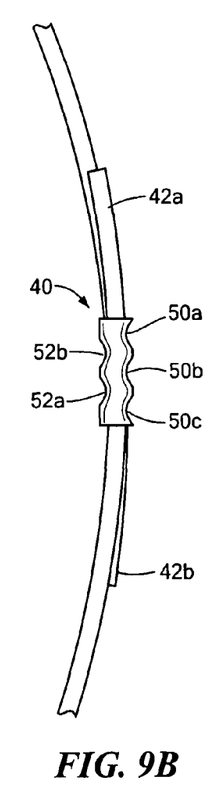
FIG. 9B is a schematic side view of the crimp tube of FIG. 7A after crimping by the crimp tool shown in FIGS. 1-4.
Figure 9C:
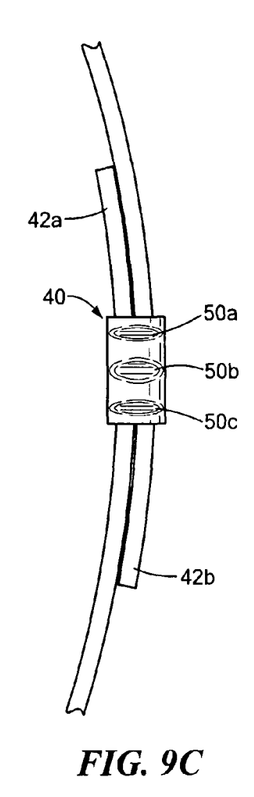
FIG. 9C is a top view of the crimp tube shown in FIGS. 7B.
Figure 9D:
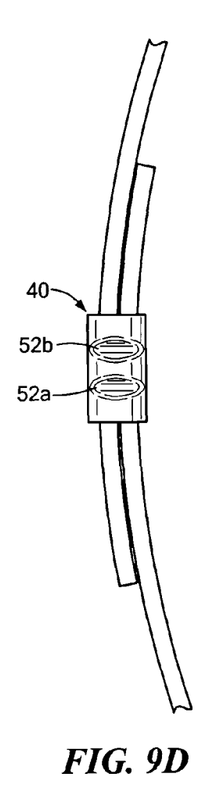
FIG. 9D is a bottom view of the crimp tube shown in FIG. 7B.

The gap between the crimping members in any embodiment may take into account the diameter of the suture and its mechanical properties and the physical dimensions of the crimp tube (its inner diameter and wall thickness) as well as the mechanical properties of the crimp tube (e.g., its hardness and tensile strength). The wave design disclosed herein of the offset opposing crimping members is such that it applies the right amount of displacement on the suture and allows a single crimping action to be used. The distance between the crimping members when the jaws are fully closed, the radius of the crimping members and the radius where the crimping members meet via the depressions are preferably designed to provide more holding power on the suture but also so that there are no stress risers on the suture due to crimping. The tip of the tool is designed to allow easier access to the surgical site and the length of the handles are such as to maximize the lever arm and minimize the amount of hand strength required to squeeze the handles. Jaws 14a and 14b may be heat treated to minimize wear after crimping. The design disclosed herein can be adjusted to work with many types of sutures (e.g., mono-filament, braided polyester, and the like). By only having to apply one crimp saves 66% of the surgeon's time when crimping. The crimp tube or clamp has a "wave" look after crimping as shown in FIG. 9B. This design allows the crimp tube to lie flat causing less tissue irritation. The typical crimp tube material is implant grade 316L stainless steel although the tube can be made from titanium. The crimping tool can also be formed from stainless steel, titanium, or the like.

Thus, although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A crimping device comprising:
    a first jaw having, across its width and extending at least partially along its length, spaced multiple fixed crimp members running lengthwise and each configured to provide a deformation on one surface of a crimp tube;
    a second jaw having, across its width and extending at least partially along its length, spaced multiple fixed crimp members running lengthwise and each configured to provide a deformation on an opposite surface of a crimp tube thereby creating a crimp pattern in a crimp tube when the first and second jaws are brought together about the crimp tube;
    a first handle for the first jaw;
    a second handle for the second jaw; and
    each jaw having a stop member defining a predefined gap between the crimp members of the first jaw and the crimp members of the second jaw when the handles are closed.

2. The crimping device of claim 1 in which the crimp members of the first jaw are offset from the crimp members of the second jaw.

3. The crimping device of claim 2 in which the first jaw has first, second, and third crimp members and the second jaw has first and second crimp members.

4. The crimping device of claim 3 in which the second crimp member of the first jaw and the first and second crimp members of the second jaw are rounded protrusions.

5. The crimping device of claim 3 in which the first and third crimp members of the first jaw are rounded protrusions.

6. The crimping device of claim 3 in which there is a first lengthwise depression between the first and second lengthwise crimp members and a second lengthwise depression between the second and third lengthwise crimp members of the first jaw.

7. The crimping device of claim 6 in which the first crimp member of the second jaw opposes the first depression of the first jaw and the second crimp member of the second jaw opposes the second depression of the first jaw.

8. The crimping device of claim 7 in which there is a first depression on one side of the first crimping member of the second jaw, a second depression between the second crimp member and the second crimp member of the second jaw, and a third depression on an opposite side of the second crimp member of the second jaw.

9. The crimping device of claim 8 in which the first crimp member of the first jaw opposes the first depression of the second jaw, the second crimp member of the first jaw opposes the second depression of the second jaw, and the third crimp member of the first jaw opposes the third depression of the second jaw.

10. The crimping device of claim 9 in which said stop members define a predefined gap of between 0.03-0.07 inches between the crimp members of the first jaw and the corresponding depressions of the second jaw and between the crimp members of the second jaw and the corresponding depressions of the first jaw when the jaws are fully closed.

11. The crimping device of claim 1 in which the handles connect to the jaws via a multiple action mechanism.

12. The crimping device of claim 1 in which the first handle includes a linkage pivotably connected between first and second handle portions.

13. The crimping device of claim 12 in which the first handle portion of the first handle is pivotably connected to the second handle and the second handle portion of the first handle is pivotably connected to the second handle.

14. A method of making a crimping device, the method comprising:
    in a first jaw, forming, across its width and extending at least partially along its length, spaced multiple crimp members running lengthwise;
    in a second jaw, forming, across its width and extending along its length, spaced multiple crimp members running lengthwise to create multiple crimps in a crimp tube when the first and second jaws are brought together about the crimp tubes;
    providing a first handle for the first jaw;
    providing a second handle for the second jaw;
    pivotably connecting the first handle to the second handle; and
    providing each jaw with a stop member defining a predefined gap between the crimp members of the first jaw and the crimp members of the second jaw when the handles are closed.

15. A crimping device comprising:
    a first moveable jaw having, across its width and extending at least partially along its length, spaced multiple fixed crimp members running lengthwise;
    a second moveable jaw having, across its width and extending partially along its length, spaced multiple fixed crimp members running lengthwise and offset from the spaced multiple fixed crimp members of the first moveable jaw; and each jaw having a stop member defining a predefined gap between the crimp members of the first jaw and the crimp members of the second jaw when the handles are closed.

16. A crimping device comprising:

a first jaw having, across its width and extending at least partially along its length, a first edge, a second middle, and a third edge crimp member each running lengthwise with a depression between the first and second crimp members and a depression between the second and third crimp members;

a second jaw having, across its width and extending at least partially along its length, first and second crimp members running lengthwise with a middle depression therebetween;

the first crimp member of the second jaw opposing one depression of the first jaw, the second crimp member of the second jaw opposing another depression of the first jaw, and the second middle crimp member of the first jaw opposing said middle depression of the second jaw; and each jaw having a stop member defining a predefined gap between the crimp members of the first jaw and the depressions of the second jaw and between the crimp members of the second jaw and the depressions of the first jaw when the jaws are closed.

17. A crimping device comprising:

a first jaw with only one lengthwise full arc crimp member, said crimp member being centrally located between a lengthwise depression on each side thereof;

a second jaw with only one full arc lengthwise depression, said depression being centrally located opposite the centrally located full arc lengthwise crimp member of the first jaw, said second jaw further including full arc lengthwise crimp members on each side of said centrally located lengthwise depression each opposing a said lengthwise depression of the first jaw;

a handle for the first jaw;

a handle for the second jaw; and a stop configured to stop the jaws from fully closing and spacing the centrally located full arc lengthwise crimp member of the first jaw from the centrally located lengthwise depression of the second jaw and spacing the full arc lengthwise crimp members of the second jaw from the lengthwise depressions of the first jaw by between 0.03-0.07 inches when the handles close.

* * * * *